United States Patent [19]

Davies et al.

[11] Patent Number: 4,642,234
[45] Date of Patent: Feb. 10, 1987

[54] DISINFECTION OF CONTACT LENSES

[75] Inventors: David J. G. Davies; Brian J. Meakin; John E. Rees, all of Bath, United Kingdom

[73] Assignee: University of Bath, Bath, United Kingdom

[21] Appl. No.: 734,270

[22] PCT Filed: Sep. 12, 1984

[86] PCT No.: PCT/GB84/00311

§ 371 Date: May 14, 1985

§ 102(e) Date: May 14, 1985

[87] PCT Pub. No.: WO85/01209

PCT Pub. Date: Mar. 28, 1985

[30] Foreign Application Priority Data

Sep. 15, 1983 [GB] United Kingdom ............... 8324781

[51] Int. Cl.⁴ .................... A61K 31/55; A61K 31/74; A61K 33/42
[52] U.S. Cl. .................................... 424/78; 424/128; 514/635; 514/840
[58] Field of Search ................. 514/634, 635; 424/78, 424/127, 128

[56] References Cited

U.S. PATENT DOCUMENTS

| Re. 29,693 | 7/1978 | Phares | 424/326 |
|---|---|---|---|
| 2,547,653 | 0/1951 | Minnis et al. | 167/59 |
| 3,694,366 | 9/1972 | Harris et al. | 252/106 |
| 3,855,140 | 12/1974 | Billany et al. | 252/106 |
| 3,888,782 | 6/1975 | Boghosian et al. | 252/106 |
| 3,908,680 | 0/1975 | Krezanoski | 134/27 |
| 3,910,296 | 0/1975 | Karageozian et al. | 134/2 |
| 3,960,745 | 6/1976 | Billany et al. | 252/106 |
| 4,029,817 | 6/1977 | Blanco et al. | 424/80 |
| 4,395,346 | 0/1983 | Kleist | 252/135 |
| 4,438,011 | 0/1984 | Howes | 252/106 |

FOREIGN PATENT DOCUMENTS

| 1150907 | 2/1983 | Canada . |
| 3007397 | 3/1981 | Fed. Rep. of Germany . |
| 2269968 | 5/1975 | France . |
| 1464333 | 9/1977 | United Kingdom . |

OTHER PUBLICATIONS

"Kinetics of a Transient Iodine Disinfecting System", by M. F. Turner et al., *British Pharmaceutical Conference*, Sheffield 1977, p. 65P, Sep. 12–14.

"Kinetics of a Transient Iodine Disinfecting System for Hydrophilic Contact Lenses", J. K. Andrews et al., *Journal of Pharmacy and Pharmacology*, British Pharmaceutical Conference 1977, p. 56P, 1977, Sep. 12–16.

*Primary Examiner*—Douglas W. Robinson
*Attorney, Agent, or Firm*—Nixon & Vanderhye

[57] ABSTRACT

Hydrophilic soft contact lenses are disinfected by soaking in a non-eye-irritant aqueous disinfecting solution obtained by the addition to tap water of a chlorhexidine salt, a sequestering agent for calcium and magnesium ions, and a dechlorinating agent. Suitably, the solution is obtained by dissolving a tablet in tap water. The preferred sequestering agent is sodium tripolyphosphate and the preferred dechlorinating agent is sodium thiosulphate. Advantageously, the chlorhexidine salt is provided in solid solution in urea to assist complete dissolution.

11 Claims, No Drawings

DISINFECTION OF CONTACT LENSES

The present invention relates to the disinfection of contact lenses and has particular, but not exclusive, application to the disinfection of hydrophilic soft contact lenses. It provides aqueous disinfecting solutions, compositions for making said solutions, and methods of disinfecting hydrophilic soft contact lenses.

Contact lenses are thin convex lenses placed directly on the eye surface to correct sight defects. There are two general categories of contact lenses, namely hard lenses and soft lenses. Hard lenses are made of glass or, more usually, hard plastics, especially cross-linked polymethylmethacrylate. Soft lenses may be made of hydrophobic plastics, especially cross-linked dimethyl polysiloxane, but usually are made of hydrophilic plastics, especially polyhydroxyethyl methacrylate cross-linked with hydroxyethyl dimethacrylate.

The disinfection of hydrophilic soft lenses using chemical agents presents a particular problem in that the lenses can absorb chemical agents from disinfecting solutions in which they are soaked. The most commonly used disinfecting solutions for soft contact lenses are aqueous solutions containing a chlorhexidine salt and it is well established that a sufficiently high concentration of chlorhexidine salt can build up in the lens to cause irritation and, sometimes, damage to the eye of the lens wearer. Accordingly, the concentration of chlorhexidine salt in the disinfecting solution should be maintained at a sufficiently low, but effective, level (below about 0.005% by weight, calculated as chlorhexidine digluconate) to reduce the risk of eye irritation. It has recently been proposed in UK Patent Specification No. 2090013A that eye irritancy resultant from chlorhexidine salt disinfection can be obviated by the use of a substantially isotonic aqueous solution containing 0.0012 to 0.003% of a chlorhexidine salt if the ionic species of the tonicity adjusting agent produces a tonicity equivalent to not more than a 0.3% solution of sodium chloride.

Prior art aqueous disinfecting solutions for hydrophilic soft lenses are made up with de-ionized, or otherwise specially purified, water thereby avoiding problems arising from hard water and chlorination if tap water was to be used. The calcium and magnesium salts in hard water would cause opaque deposits to build up on the lens. Further, chlorine would be absorbed and concentrated in the lens in the same manner as chlorhexidine salt discussed above. Whilst there have been theoretical proposals to provide chlorhexidine salt-containing tablets for dissolution to form the aqueous disinfecting solutions, to the best of our knowledge and belief, chlorhexidine salt-containing solutions have always been supplied to the user ready made up.

The term "tap water" is used herein to mean water which has not been de-ionized or specially purified but is sufficiently uncontaminated by impurities to be of a potable standard. Typically such water is supplied as drinking water from treatment plants through mains to a tap or faucet. However, the term is not restricted to water supplied from a tap or faucet and includes water of equivalent quality from other sources.

It is an object of the present invention to provide an aqueous disinfecting solution for hydrophilic contact lenses made up with tap water, which solution does not cause opaque deposits on the lens and is non-irritant to the eye of the wearer. It is another object to provide a tablet, or other solid formulation, of a composition which can be dissolved in tap water to provide such a disinfecting solution.

According to a first aspect of the present invention, there is provided a non-eye-irritant disinfecting solution for hydrophilic soft contact lenses, said solution being obtained by the addition to tap water (as hereinbefore defined) of:
an ophthalmically acceptable chlorhexidine salt;
a sequestering agent for calcium and magnesium cations; and
a dechlorinating agent.

According to a second aspect of the present invention, there is provided a composition for addition to tap water (as hereinbefore defined) to provide a non-eye-irritant aqueous disinfecting solution for hydrophilic soft lenses, said composition comprising:
an ophthalmically acceptable chlorhexidine salt;
a sequestering agent for calcium and magnesium cations; and
a dechlorinating agent.

It is preferred that said composition is in the form of a solid formulation, for example, a capsule, granules, powder or, especially, a tablet. However, the composition can be in the form of a concentrated solution. In both cases, it is preferred that the composition is such as to provide the required disinfecting solution when added to 10 ml tap water.

According to a third aspect of the present invention, there is provided a method of disinfecting a hydrophilic soft lens which comprises soaking the lens in a non-eye-irritant aqueous disinfecting solution obtained by the addition to tap water (as hereinbefore defined) of:
an ophthalmically acceptable chlorhexidine salt;
a sequestering agent for calcium and magnesium cations; and
a dechlorinating agent.

The lens will be soaked for a sufficient time to provide the required disinfection. Usually, it will be soaked for several hours, more usually overnight. However, the lens also can be soaked for a shorter period when it has been temporarily removed from the eye for some purpose other than routine disinfection, such as during a sight test or when swimming.

The disinfecting solution contains an antimicrobial concentration of an ophthalmically acceptable chlorhexidine salt, which concentration is insufficient to cause irritancy to the eye. Suitably, said concentration (calculated as chlorhexidine digluconate) is in the range 0.001 to 0.005% by weight, usually 0.003 to 0.005% by weight, and preferably 0.004% by weight.

In the preferred composition for addition to 10 ml tap water, said concentrations correspond to a chlorhexidine salt content (calculated as chlorhexidine digluconate) of 0.0001 to 0.0005 g, 0.0003 to 0.0005g, and 0.0004 g respectively.

The disinfecting agent is chlorhexidine (i.e. 1,6-di(4'-chlorophenyldiguanido)hexane) in the form of an ophthalmically acceptable acid addition salt thereof such as the dihydrochloride or, preferably, the diacetate or, especially, digluconate.

The sequestering agent is used in an amount sufficient to remove calcium and magnesium ions from the tap water vehicle of the disinfecting solution. Whilst the minimum amount required will vary depending upon the hardness of the tap water, an amount of at least 0.1% by weight usually will be used. Suitably, the amount will be in the range 0.1 to 1% by weight, usually 0.2 to 0.8% by weight, and especially 0.3 to 0.6% by weight. In the preferred composition for addition to 10 ml tap water, said concentrations correspond to 0.01 to 0.1 g, 0.02 to 0.08g and 0.03 to 0.06 g respectively.

The sequestering agent can be any compound which will sequester at least calcium and magnesium ions from tap water and which is compatible with the other components, and ophthalmic use of the disinfecting solution. In particular, the sequestering agent must be non-irritant to the eye at the concentrations used in the solution. Preferably, the sequestering agent is a complex polyphosphate, e.g. sodium hexametaphosphate, sodium pyrophosphate or, especially, sodium tripolyphosphate.

The dechlorinating agent is used in an amount which prevents chlorine transference from water chlorination via the lens to the eye. The minimum amount required will vary depending upon the extent of chlorination of the tap water but usually 0.001% by weight will be sufficient. Suitably, the amount will be in the range 0.001 to 1% by weight, usually 0.005 to 0.1% by weight, especially about 0.01%. These concentrations correspond to 0.0001 to 0.1 g, 0.0005 to 0.01 g, and 0.001 g respectively in the preferred composition for addition to 10 ml tap water.

The dechlorinating agent can be any compound which will remove chlorine from tap water and which is compatible with the other components, and ophthalmic use, of the disinfectant solution. In particular, the dechlorinating agent must be non-irritant to the eye at the concentrations used in the solution. Preferably, the dechlorinating agent is sodium metabisulphite, sodium sulphite or, especially, sodium thiosulphate. The sodium thiosulphate can be added in the form of its pentahydrate but preferably is added in its anhydrous form.

The solution may contain other components conventionally present in disinfecting solutions for hydrophilic soft contact lenses. In particular, it can contain an acid (to adjust the pH) and/or a tonicity adjusting agent.

The acid usually will be present in an amount sufficient to provide the solution with a pH in the range 4.0 to 8.0, preferably 5.5 to 8.0, especially 6.0 to 7.5. Having regard to the composition aspect of the invention, it is preferred that the acid is a solid. suitable acids include fumaric, citric, meleic, adipic and, preferably, malic acid. If required, the solution can be buffered to the required pH.

Usually, the composition of the disinfectant solution will be selected to be substantially isotonic but the isotonicity may be provided by components present in the solution for other purposes. If it is required to use a tonicity adjusting agent, sodium chloride can be used.

It is especially preferred that the disinfecting solution of the invention contain a solution-enhancing system comprising urea and a non-ionic surfactant.

Chlorhexidine is incompatible with certain sequestering agents, including the preferred complex polyphosphates, in that a clear solution is not obtained when both are dissolved in tap water at the same time. It has been found that this problem can be overcome by adding the chlorhexidine (or salt thereof) in solution in urea together with a non-ionic surfactant. Usually, the chlorhexidine will be dissolved in molten urea, the resultant solution cooled and then granulated. Suitably, urea is used in an amount of 0.5 to 2% by weight, preferably 1 to 1.6% by weight. In the preferred composition to be added to 10 ml tap water, said concentrations correspond to 0.05 to 0.2 g and 0.1 to 0.16 g respectively. Urea affects the tonicity of the solution and hence the amount of urea used usually will be limited to that which will result in tonicity.

Suitable non-ionic surfactants for use with urea in the solution-enhancing system include polyoxyethylene alkyl ethers, polyoxyethylene alkyl phenyl ethers, and polyoxyethylene sorbitan and other sugar-based alkyl esters. Presently preferred surfactants are polyethylene glycol monocetyl ethers (e.g. Cetomacrogols), polyoxyethylene (20) sorbitan monooleate (e.g. Polysorbate 80), sucrose monostearate, nonylphenolethoxylate (e.g. available under the Trade Marks "Antarox CO-630"and "EMPILAN N92"), and, especially, polyoxyethylene (20) stearyl ether (e.g. available under the Trade Mark "Brij 78").

As previously stated the compositions of the present invention preferably are in tablet form. Such tablets are manufactured using conventional techniques optionally with the addition of conventional tableting additives such as lubricants in such amounts as are required to provide tablets of the desired strength and dissolution profile. Suitable additives include polyvinyl pyrrolidone (PVP) the polyethylene glycol (PEG).

The invention is illustrated in the following non-limiting Examples.

EXAMPLE 1

A tablet was prepared by conventional tableting technique from the following:
Sodium pyrophosphate: 0.04 g
*Chlorhexidine digluconate
(20% aqueous solution): 0.002 ml
Sodium thiosulphate: 0.001 g
Sodium Chloride: 0.09 g
Polysorbate 80: 0.001 g
(Tween 80)
Malic Acid: 0.005 g
*Equivalent 0.0004 g chlorhexidine digluconate.

When dissolved in 10 ml tap water, the tablet provided a solution effective for the disinfection of hydrophilic soft contact lenses on soaking overnight.

EXAMPLE 2

A tablet was prepared by conventional tableting technique from the following:
Sodium hexametaphosphate: 0.04 g
*Chlorhexidine diacetate: 0.003 g
Sodium metabisulphite: 0.005 g
Urea: 0.15 g
Cetomacragol: 0.0025 g
Malic Acid: 0.005 g
*Equivalent 0.0004 g chlorhexidine digluconate.

The chlorohexidine diacetate was dissolved in the (molten) urea and the resultant solution cooled and granulated before addition to the other tablet ingredients.

When dissolved in 10 ml tap water, the tablet provided a solution effective for the disinfection of hydrophilic soft contact lenses on soaking overnight.

EXAMPLE 3

A tablet was prepared by conventional tableting technique from the following:
Sodium tripolyphosphate: 0.04 g
*Chlorhexidine digluconate: 0.002 ml
(20% aqueous solution )
Sodium thiosulphate: 0.001 g
Urea: 0.15 g
Brij 78: 0.001 g Malic Acid: 0.005 g

*Equivalent to 0.0004 g chlorhexidine digluconate.

The chlorhexidine digluconate was dissolved in the (molten) urea and the resultant solution cooled and granulated before addition to the other tablet ingredients.

What is claimed is:

1. A solid composition for addition to tap water to provide a non-eye irritant aqueous disinfecting solution for hydrophilic soft contact lenses, said composition comprising:
    an antimicrobial effective amount of an opthalmically acceptable chlorhexidine salt;
    an opthalmically acceptable polyphosphate sequestering agent for calcium or magnesium cations in an amount effective to sequester said ions from tap water; and
    an opthalmically acceptable metabisulphite, sulphite or thiosulphate dechlorinating agent in an amount effective to remove chlorine from a solution of the chlorhexidine salt in tap water.

2. A composition as claimed in claim 1, which is in the form of a tablet.

3. A composition as claimed in claim 1, containing 0.0003 to 0.0005 g of chlorhexidine salt (calculated as chlorhexidine digluconate); 0.02 to 0.08 g of the sequestering agent; and 0.0005 g to 0.01 g of the dechlorinating agent.

4. A composition as claimed in claim 1, wherein the chlorhexidine salt is selected from chlorhexidine diacetate and chlorhexidine digluconate; the sequestering agent is selected from sodium hexametaphosphate, sodium pyrophosphate or sodium tripolyphosphate, and the dechlorinating agent is selected from sodium metabisulphate, sodium sulphite and sodium thiosulphate.

5. A composition as claimed in claim 1, containing an acid selected from fumaric, citric, maleic, adipic or malic acid in an amount effective to provide the solution with a pH in the range of 4.0 to 8.0.

6. A composition as claimed in claim 1 containing sodium chloride as a tonicity adjusting agent to provide isotonicity.

7. A composition as claimed in claim 1 containing an amount sufficient to enhance dissolution of the solid composition on addition to tap water of a system comprising urea and a non-ionic surface active agent selected from polyoxyethylene alkyl ethers, polyoxyethylene alkyl phenyl ethers, polyoxyethylene sorbitan and other sorbitan and sucrose alkyl esters.

8. A composition as claimed in claim 7 containing 0.1 to 0.16 g urea.

9. A tablet for addition to 10 ml tap water to provide a non-eye irritant aqueous disinfecting solution for hydrophilic soft contact lenses, said composition comprising:
    0.0003 to 0.0005 g of an opthalmically acceptable chlorhexidine salt, calculated as chlorhexidine digluconate;
    0.002 to 0.8 g of a polyphosphate sequestering agent for calcium or magnesium cations; and
    0.0005 to 0.01 g of metabisulphite, sulphite or thiosulphate dechlorinating agent.

10. A tablet for addition to 10 ml tap water to provide a non-eye irritant aqueous disinfecting solution for hydrophilic soft contact lenses, said composition comprising:
    0.0003 to 0.0005 g of an opthalmically acceptable chlorhexidine salt, calculated as chlorhexidine digluconate, in a solid solution in 0.1 to 0.16 g urea;
    0.002 to 0.08 g of a polyphosphate sequestering agent for calcium or magnesium cations;
    0.0005 to 0.01 of a metabisulphite, sulphite or thiosulphate dechlorinating agent; and
    an amount sufficient to enhance dissolution of the tablet on addition to tap water of a non-ionic surface active agent selected from polyoxyethylene alkyl ethers, polyoxyethylene alkyl phenyl ethers, polyoxyethylene sorbitan and other sorbitan and sucrose alkyl esters.

11. A method for disinfecting a hydrophilic soft contact lens which comprises the steps of:
    (1) dissolving the tablet of claim 2 in a volume of tap water to provide a non-eye irritant aqueous disinfecting solution; and
    (2) soaking a hydrophilic soft lens in the solution formed in step (1) for a sufficient time to disinfect the lens.

* * * * *